United States Patent [19]

de Sousa et al.

[11] 4,283,444
[45] Aug. 11, 1981

[54] METHOD OF PROTECTING KERATINOUS MATERIAL FROM ATTACK BY INSECTS THAT FEED ON KERATIN BY TREATMENT WITH 5-PHENYLCARBAMOYLBARBITURIC ACID COMPOUNDS

[75] Inventors: Bernardo de Sousa, Basel; René Muntwyler, Hofstetten; Werner Schmid, Riehen, all of Switzerland

[73] Assignee: Ciba-Geigy Corporation, Ardsley, N.Y.

[21] Appl. No.: 73,048

[22] Filed: Sep. 6, 1979

[30] Foreign Application Priority Data

Sep. 12, 1978 [CH] Switzerland .................. 9545/78

[51] Int. Cl.³ ............................................ A01N 43/54
[52] U.S. Cl. .................................. 427/421; 424/228; 424/254; 427/428; 427/430.1; 428/907; 544/301
[58] Field of Search ............... 544/301; 424/254, 228; 427/421, 428, 430.1

[56] References Cited

U.S. PATENT DOCUMENTS 3,961,061  6/1976  Kramer et al. .................. 544/301

FOREIGN PATENT DOCUMENTS 39-1445  2/1964  Japan ............................... 544/301

OTHER PUBLICATIONS

Waterhouse, "Wool Digestion and Mothproofing", in Advances in Pest Control Research, vol. II, pp. 208–212, ed. by Medcalf, pub. Interscience (1958).
Beriger, Chemical Abstracts, 88:62412m, (1978).

Makizawa et al., Chemical Abstracts, 86:134902e (1977).

Primary Examiner—Paul M. Coughlan, Jr.
Attorney, Agent, or Firm—Edward McC. Roberts; John P. Spitals

[57] ABSTRACT

A method of protecting keratinous material, especially wool, from attack by insects that feed on keratin, which comprises treating said material with compounds of the formula

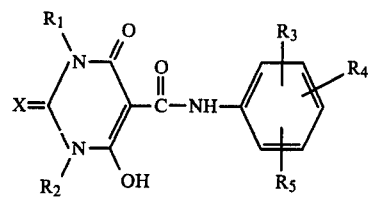

wherein X is oxygen or sulfur, each of $R_1$ and $R_2$ independently is alkyl, alkenyl, benzyl or unsubstituted or substituted phenyl, $R_3$ is halogen, nitro or trihalomethyl, $R_4$ is hydrogen, halogen or trihalomethyl, and $R_5$ is hydrogen, halogen, methyl or methoxy. The invention also provides novel compounds of the formula (1) wherein at least one of $R_1$ and $R_2$ is phenyl or substituted phenyl and X is oxygen as well as compositions containing the compounds of the formula (1) and compositions which, in addition to the compounds of formula (1), also contain synthetic pyrethroids, esters of α-alkyl-substituted phenylacetic acids or substituted sulfanilides.

19 Claims, No Drawings

METHOD OF PROTECTING KERATINOUS MATERIAL FROM ATTACK BY INSECTS THAT FEED ON KERATIN BY TREATMENT WITH 5-PHENYLCARBAMOYLBARBITURIC ACID COMPOUNDS

The present invention relates to a method of protecting keratinous material, in particular wool, woollen goods, hides, furs and feathers, from attack by insects that feed on keratin and from feeding damage, especially from attack by moths, beetles and other pests that feed on keratin, which comprises treating said keratinous substrates with specific 5-phenylcarbamoylbarbituric and -thiobarbituric acid compounds, and to compositions containing these compositions as well as to novel 5-phenylcarbamoylbarbituric acid compounds.

5-Phenylcarbamoylbarbituric acid compounds and the use thereof for controlling insects which are harmful to plants and animals, especially their use as field insecticides, are known from German Offenlegungsschrift 2 719 777. German Offenlegungsschrift 2 405 733 discloses 5-phenylcarbamoylthiobarbituric acid compounds and the use thereof as pesticides in plant protection; and German Offenlegungsschrift 2 405 732 teaches the use of such 5-phenylcarbamoylthiobarbituric acid compounds as ecto- and endoparasiticides.

Surprisingly, it has now been found that a selected group of 5-phenylcarbamoylbarbituric and -thiobarbituric acid compounds, namely those of the formula

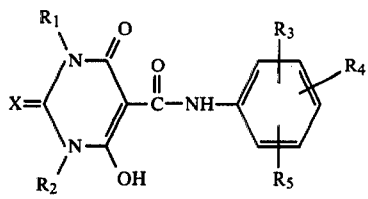

wherein X is oxygen or sulfur, each of $R_1$ and $R_2$ independently is alkyl of 1 to 4 carbon atoms, alkenyl of 3 or 4 carbon atoms, benzyl or unsubstituted or substituted phenyl, $R_3$ is halogen, nitro or trihalomethyl, $R_4$ is hydrogen, halogen or trihalomethyl, and $R_5$ is hydrogen, halogen, methyl or methoxy, and the tautomeric forms and salts thereof, are most suitable for use as protectants against insects that feed on keratin, for example moths and beetles.

Accordingly, the present invention provides a method of protecting keratinous material from attack by insects that feed on keratin and from feeding damage caused by such insects, which comprises treating the material to be protected with compounds of formula (1). The invention also relates to the use of compounds of formula (1) as protectants for keratinous material against insects that feed on keratin, and to the material proofed with compounds of the formula (1).

A substituted phenyl radical $R_1$ and $R_2$ in formula (1) preferably carries one to three substituents selected from the group consisting of alkyl or alkoxy, each of 1 to 4 carbon atoms, chlorine, bromine, fluorine, nitro or trihalomethyl, but at most one nitro group and at most two trihalomethyl and alkoxy groups. The term "halogen" comprises all halogen atoms, but preferably chlorine, bromine or fluorine.

In the process of the present invention, both compounds in which X is oxygen and those in which X is sulfur can be employed with good results; however, compounds in which X is oxygen are preferred.

The process of the invention can be carried out with particular advantage using compounds of the formula

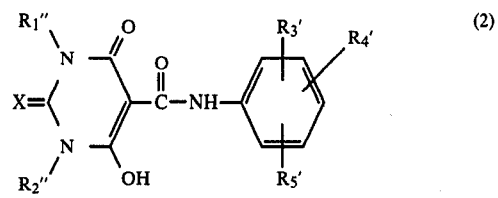

and the tautomers and salts thereof, wherein X is oxygen or sulfur, each of $R_1''$ and $R_2''$ independently is methyl, ethyl, allyl or a group of the formula

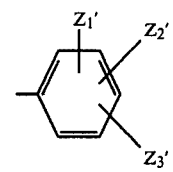

wherein $Z_1''$ is hydrogen, chlorine, bromine, methyl, methoxy, ethoxy, —$CF_3$ or nitro, $Z_2'$ is hydrogen, chlorine, bromine, methyl or —$CF_3$, $Z_3'$ is hydrogen, chlorine or methyl, $R_3'$ is chlorine, bromine or —$CF_3$, $R_4'$ is hydrogen, chlorine or bromine, and $R_5'$ is hydrogen, bromine, methyl or methoxy.

Within the scope of the formula (2), preferred compounds are those in which $R_1''$ and $R_2''$ are the same, in particular those in which $R_1''$ and $R_2''$ are methyl, $R_3'$ is —$CF_3$, chlorine or bromine, $R_4'$ is chlorine or hydrogen and $R_5'$ is hydrogen.

Within the scope of the formula (2), both compounds in which X is oxygen and those in which X is sulfur are effective. Preferred compounds in this connection are also those in which X is oxygen.

The compounds of formula (1) exist in different tautomeric forms (keto/enol tautomerism), for example in accordance with the following scheme:

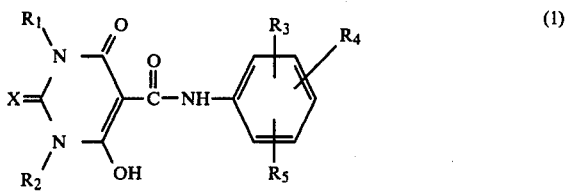

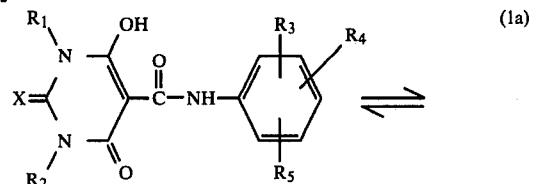

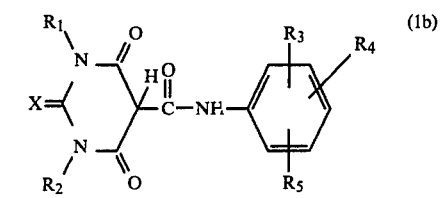

All tautomeric forms and mixtures thereof can be employed in the process of the invention. Accordingly, the individual formulae also comprise the respective possible tautomeric forms.

The compounds of formula (1) can also be used in the process of the invention in the form of their salts. Such salts are in particular the alkali metal, ammonium or amine salts, preferably the sodium, potassium, ammonium or alkylamine, especially triethylamine, salts.

The compounds of formula (1), including the tautomers and salts thereof, used in the process of the invention possess an excellent action against insects that feed on keratin, for example against Lepidoptera larvae, such as Tineola spec. and Tinea spec., and against Coleoptera larvae, for example Anthrenus spec. and Attagenus spec. The compounds of formula (1) are preeminently suitable for proofing keratinous material against feeding damage by insects, especially for providing such material with a washfast and lightfast protective finish against insects, in particular moths and beetles. The keratinous material to be proofed can be both in the raw and in the processed state, for example raw or processed sheep's wool or products made of other animal hairs, hides, furs and feathers.

A particularly important feature of the compounds of formula (1) used in the method of the invention is their action against the larvae of the webbing clothes moth (*Tineola bisselliella*) and common clothes moth (*Tinea pellionella*) as well as against the larvae of the fur beetle and carpet beetle (Attagenus spec. and Anthrenus spec. respectively).

In this connection, particular attention is to be drawn to the fact that the action against beetles that feed on keratin (and their larvae), e.g. against Attagenus spec. and especially Anthrenus spec., is most pronounced and far more potent than the action e.g. against moths. This feature, which is most surprising, can be accordingly taken into account in practical application.

The method of the present invention is therefore preferably used on the one hand for protecting woollen textiles, for example blankets, wool carpets, woollen underwear, woollen clothing and knits, and also blends, one component of which is wool, for example blends of wool and other natural fibres, preferably cotton, or of wool and synthetic fibers, and, on the other hand, also for protecting furs and skins from attack by the above-mentioned pests.

The compounds of formula (1) are applied to the above substrates, in particular to woollen textiles and wool blends, preferably by methods commonly known and employed in dyeing, such as the exhaust method and padding. To this end, an aqueous dispersion (or emulsion or suspension) of the respective active substance is prepared. The active substance is preferably dissolved beforehand in an organic solvent, such as an aliphatic or alicyclic alcohol, a ketone, a hydrocarbon, such as benzene, a xylene, toluene, petroleum distillate, and also a chlorinated or fluorinated hydrocarbon, especially in propylene glycol, methoxy ethanol, ethoxy ethanol or dimethyl formamide, and then added to the treatment bath, which can contain additional assistants conventionally used in dyeing, for example dispersants. The organic stock formulation can already contain such assistants.

The aqueous dispersions contain, for example, surfactants, for example anionic compounds, such as soaps and other carboxylates (e.g. alkali metal salts of higher fatty acids), derivatives of sulfur oxyacids (e.g. the sodium salt of dodecylbenzenesulfonic acid, water-soluble salts of sulfuric acid monoesters of higher-molecular alcohols or of their polyglycol ethers, for example soluble salts of dodecyl alcohol sulfate or of dodecyl alcohol polyglycol ether sulfate), derivatives of phosphorus oxyacids (e.g. phosphates), derivatives with acid (electrophilic) nitrogen in the hydrophilic group (e.g. disulfine salts), cationic surface-active agents, such as amines and their salts (e.g. lauryldiethylenetriamine), onium compounds, amine oxides or nonionic surface-active agents, such as polyhydroxy compounds, surface-active agents based on mono- or polysaccharides, higher molecular acetylene glycols, polyglycol ethers (e.g. polyglycol ethers of higher fatty alcohols, polyglycol ethers of higher molecular alkylated phenols). The liquor can additionally contain further conventional assistants, such as water-soluble perborates, polyphosphates, carbonates, silicates, fluorescent whitening agents, plasticisers, salts with acid reaction, such as ammonium or zinc silicofluoride, or certain organic acids, such as oxalic acid, acetic acid or, in particular, formic acid, and also antimicrobial agents and finishing agents, for example those based on synthetic resins or starch.

The textile material can be impregnated, for example, with the active substances by means of dye, bleaching, chroming or aftertreatment baths, whilst various textile finishing methods are possible, for example the pad or exhaust method.

The treatment is carried out advantageously at temperatures from 10° to 100° C., for example at 10° to 70° C., but preferably at about 20° to 60° C.

Because of their good solubility in organic solvents, the active compounds of formula (1) can also be very easily applied from non-aqueous media to the substrates to be protected (solvent application). Suitable solvents in this connection are, inter alia, trichloroethylene, methylene chloride, hydrocarbons, propylene glycol, methoxy ethanol, exthoxy ethanol, dimethyl formamide, to which dispersing agents (e.g. emulsifiers, such as sulfated castor oil, fatty alcohol sulfates etc.) and/or other assistants can be added. The material to be protected is usually simply impregnated with these solutions.

The proofing of the material to be protected can also be combined with a dry cleaning process. To this end, the active compounds are dissolved in the cleansing agent (such as a lower halogenated alkane, for example trichloroethylene etc.) and the cleaning process is carried out in the usual manner.

However, the active compounds can also be dissolved in readily volatile organic solvents and the resulting solution then sprayed onto the substrate (spray application). Textile fabrics, furs and feathers are in particular suitable for this application. The advantage of the spray application is that pollution of the wastewaters is avoided on account of the recovery of the solvent.

In the method of the present invention, the compounds of formula (1) can also be used in combination with other protectants which act against insects that feed on keratin, for example with urea derivatives, benzimidazoles, aromatic sulfonamides and phosphoric and phosphonic esters.

The amount of compound of formula (1) employed depends on the respective substrate and the method of application. However, it is ordinarily such that, after application to the material which it is desired to protect, the latter contains about 10 to 2000 ppm, preferably 100 to 1000 ppm, of active ingredient, in which connection the upper limit is largely determined by economic considerations, whereas the lower limit depends on criteria such as the intended breadth and permanency of the protective action, but especially on whether the compounds of formula (1) are applied alone or in combination with other active compounds. This corresponds, for example, to concentrations of 0.001 to 1 g/l of treatment bath, depending on the degree of exhaustion, when the compounds of formula (1) are applied by the exhaust method at a liquor ratio of 1:20. When application is by the pad method, concentrations of up to 2 g/l are possible.

The compounds of formula (1) can also be employed in combination with other compounds having similar action. As the compounds of formula (1) are particularly effective against beetle larvae, e.g. of the species Attagenus and Anthrenus (see above), they can be employed in the method of the invention together with those moth and beetle preventives which are less effective against beetles, e.g. Attengenus and Anthrenus, but which instead are particularly effective against other pests that feed on keratin, e.g. moths. Such methods also fall within the scope of the present invention. A more effective and broader protection is thus obtained. Compounds with which the compounds of formula (1) can be employed jointly in the method of the present invention are e.g. the following pyrethroids, especially those of the following classes:

(1) Compounds of the formula

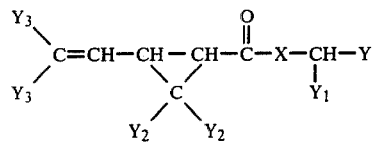

(3)

wherein X is oxygen or sulfur, $Y_1$ is hydrogen, CN, $CH_3$, $C_2H_5$, i-$C_3H_7$,

—C≡CH, —C≡C—$C_6H_5$, —C≡C—$CH_3$, —CH=$CH_2$, —CH=CH—$CH_3$, —$CH_2$—CH=$CH_2$ or —$CH_2$—CH=CHCl, $Y_2$ is methyl or both of $Y_2$ together complete a cyclopropane, cyclobutane or cyclopentane ring, $Y_3$ is chlorine, bromine, fluorine, $CF_3$ or methyl, and Y is

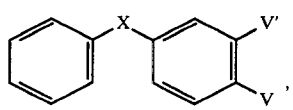

wherein V is hydrogen, chlorine, bromine, fluorine, $CH_3$ or $NO_2$, or V' is $CF_3$ if V is hydrogen, and X is as defined above; or Y is

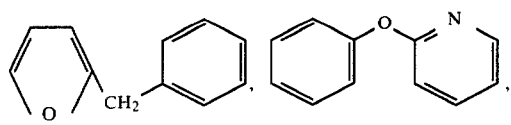

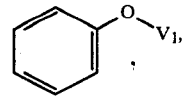

wherein $V_1$ is —$CH_2$—CH=$CH_2$, $CH_2$—C≡CH, —$CH_2$—CH=CH—$CH_3$,

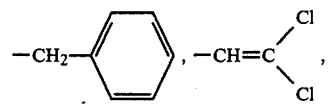

CF=CFCl, or —CF=$CF_2$, or Y is

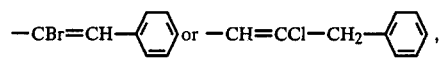

in particular compounds of the class of the 3-(2',2'-dihalovinyl)-2,2-dimethylcyclopropanecarboxylic acid -3''-phenoxybenzyl esters, e.g. a compound of the formula

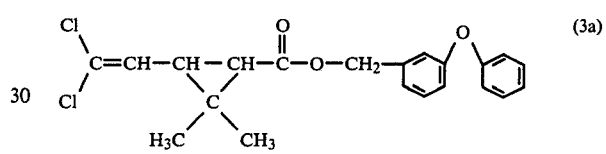

(3a)

known from J. Text. Inst. 1976, No. 3, Vol. 67, 77, wherein both chlorine atoms can also be replaced by bromine atoms.

(2) Compounds of the above formula (3) in which the

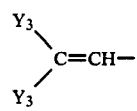

group can be replaced by the following groups: $Br_2C$=CBr—,

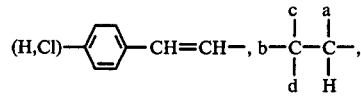

wherein each of a, b, c and d independently is chlorine, bromine or fluorine, whilst c and d can also be methyl, Cl—C≡C—,

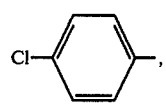

$(CH_3)_3C$—O—, $CH_2$=CH—$CH_2$—O—, and also a number of selected groups which stem from the Examples relating to mixture preparations. Preferred compounds of this group are those of the class of 3-(1',2',2',2'-tetrahaloethyl)-2,2-dimethylcyclopropanecarboxylic acid 3''-phenoxybenzyl esters disclosed in Swiss patent application 6384/78, in particular compounds of the formula

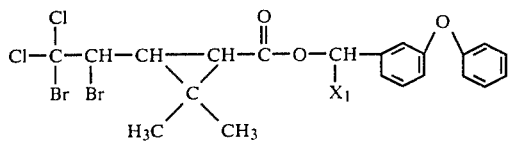

wherein $X_1$ is hydrogen, CN or —C≡CH.

(3) Compounds of the formula

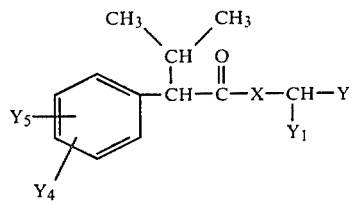

wherein X, Y and $Y_1$ are as defined above, $Y_4$ is hydrogen, $CH_3$, chlorine, $NO_2$, CN, $OCH_3$,

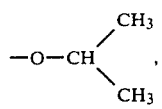

—O—$CH_2$—C≡CH or —O—$CH_2$—CH=$CH_2$, and $Y_5$ is hydrogen, $CH_3$, chlorine, bromine or fluorine, as well as a number of special compounds of this type which stem from the Examples relating to mixture preparations.

Preferred compounds of this group are those of the class of α-phenyl-α-isopropylacetic acid 3'-phenoxybenzyl esters disclosed in Swiss patent application 7381/78, in particular compounds of the formula

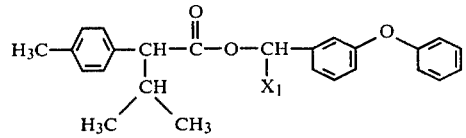

wherein $X_1$ is hydrogen, CN or —C≡CH.

(4) Compounds of the formula

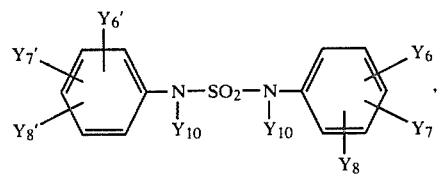

wherein each of $Y_6$, $Y_7$, $Y_8$, $Y_6'$, $Y_7'$ and $Y_8'$ independently is hydrogen, chlorine, bromine, fluorine or $CF_3$, whilst each phenyl nucleus carries at least one substituent which is different from hydrogen and $Y_{10}$ is alkyl or aralkyl, in particular $CH_3$, $C_2H_5$, n—$C_3H_7$, n—$C_4H_9$, i—$C_3H_7$, t—$C_4H_9$ and $CH_2$—$C_6H_5$.

The combination of active compounds can be employed in the same manner as described for the compounds of formula (1).

The invention also provides compositions for carrying out the method of the invention which contain compounds of formula (1). These compositions can addi-tionally contain conventional formulation agents, such as wetting agents, dispersants and emulsifiers, and optionally water or solvents as mentioned in the description of the method. The compositions can also additionally contain one or more of the compounds listed above under (1) to (5), in which connection combination preparations for moth- and beetle-proofing also fall within the scope of the present invention.

Some of the active compounds of formula (1) are known. Novel compounds, however, are those of the formula

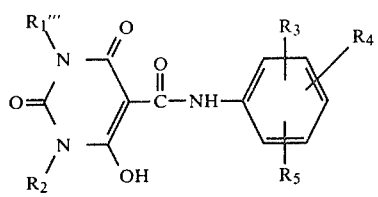

wherein $R_1'''$ is unsubstituted or substituted phenyl, $R_2$ is alkyl of 1 to 4 carbon atoms, alkenyl of 3 or 4 carbon atoms, benzyl or unsubstituted or substituted phenyl, $R_3$ is halogen, nitro or trihalomethyl, $R_4$ is hydrogen, halogen or trihalomethyl, and $R_5$ is hydrogen, halogen, methyl or methoxy, and the tautomeric forms and salts thereof.

These novel compounds of formula (6) likewise fall within the scope of the present invention. Possible substituents of phenyl radicals $R_1'''$ and $R_2$ are preferably one or two substituents selected from the group consisting of alkyl or alkoxy, each of 1 to 4 carbon atoms, chlorine, bromine, fluorine, nitro or trihalomethyl, but at most one nitro group.

The term "halogen" is to be understood as comprising all halogen atoms, but preferably chlorine, bromine or fluorine.

Examples of such compounds are those of the formula

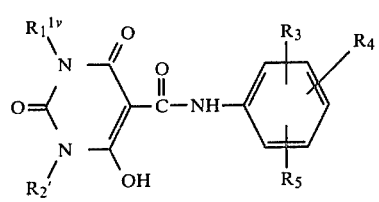

wherein $R_1^{iv}$ is a group of the formula

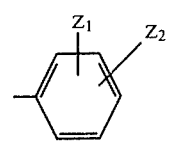

wherein $Z_1$ is hydrogen, chlorine, bromine, fluorine, alkyl or alkoxy, each of 1 to 4 carbon atoms, trihalomethyl or nitro, and $Z_2$ is hydrogen, chlorine, bromine, fluorine, alkyl or alkoxy, each of 1 to 4 carbon atoms, or trihalomethyl, $R_2'$ is alkyl of 1 to 4 carbon atoms, alkenyl of 3 or 4 carbon atoms, benzyl or a group of the formula

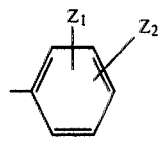

wherein $Z_1$ is hydrogen, chlorine, bromine, fluorine, alkyl or alkoxy, each of 1 to 4 carbon atoms, trihalomethyl or nitro, and $Z_2$ is hydrogen, chlorine, bromine, fluorine, alkyl or alkoxy, each of 1 to 4 carbon atoms, or trihalomethyl, and $R_3$, $R_4$ and $R_5$ are as defined for formula (6), and the tautomeric forms and salts thereof.

Interesting compounds of formula (6) are those of the formula

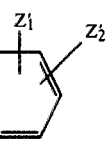
(7)

wherein $R_1^v$ is a group of the formula

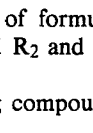

wherein $Z_1'$ is hydrogen, chlorine, bromine, methyl, methoxy, ethoxy, —$CF_3$ or nitro, and $Z_2'$ is hydrogen, chlorine, bromine, methyl or —$CF_3$; $R_2''$ is methyl, ethyl, allyl or a group of the formula

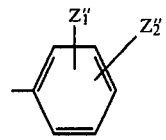

wherein $Z_1'$ is hydrogen, chlorine, bromine, methyl, methoxy, ethoxy, —$CF_3$ or nitro, and $Z_2'$ is hydrogen, chlorine, bromine, methyl or —$CF_3$; $R_3'$ is chlorine, bromine or —$CF_3$, $R_4'$ is hydrogen, chlorine or bromine and $R_5'$ is hydrogen, chlorine, bromine, methyl or methoxy, and the tautomeric forms and salts thereof.

Preferred compounds of formulae (6) and (7) are those in which $R_1'''$ and $R_2$ and $R_1^v$ and $R_2'$ are the same.

Particularly interesting compounds are those of the formula

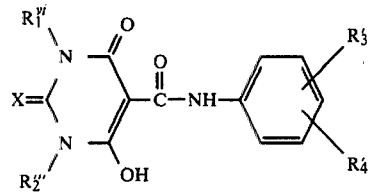
(7a)

wherein $R_1^{vi}$ is a group of the formula

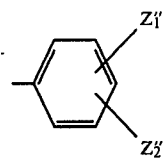

wherein $Z_1''$ is hydrogen, chlorine or —$CF_3$ and $Z_2''$ is hydrogen or chlorine; $R_2'''$ is methyl, ethyl or a group of the formula

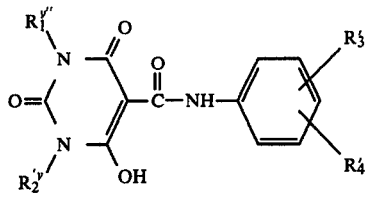

wherein $Z_1''$ and $Z_2''$ are as defined above; $R_3'$ is chlorine, bromine or —$CF_3$ and $R_4'$ is hydrogen, chlorine or bromine, and the tautomeric forms and salts thereof, in particular those compounds of the formula (8)

wherein $R_1^{v'}$ is phenyl, p-chlorophenyl or m-chlorophenyl and $R_2'^v$ is methyl, ethyl, phenyl, p-chlorophenyl or m-chlorophenyl, and $R_3'$ and $R_4'$ are as defined for formula (7a), and the tautomeric forms and salts thereof.

It will be understood that the formulae (6) to (8) also comprise the tautomeric forms and salts of the aforementioned compounds, and also accordingly fall within the scope of the invention.

The compounds of formula (1) employed in the process of the present invention, in which X is sulfur, are known from German Offenlegungsschrift 2 405 732 and 2 405 733 and can be obtained by the methods described therein. Those compounds of the formula (1), in which X is oxygen and both $R_1$ and $R_2$ are different from phenyl, are known from German Offenlegungsschrift 2 719 777 and can be obtained by the methods described therein.

The novel compounds of formula (6) can be obtained by methods analogous to those described in German Offenlegungsschrift 2 719 777, for example by reaction of a correspondingly substituted barbituric acid of the formula

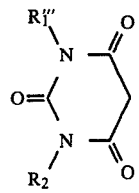
(9)

with a phenyl isocyanate of the formula

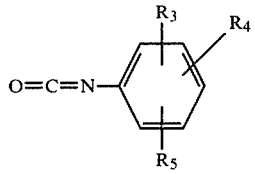

(10)

in which formulae (9) and (10) the general symbols are as defined for formula (6), the reaction being carried out in the temperature range between 0° and 200° C., preferably in an inert solvent or diluent and under the conditions defined in the cited Offenlegungsschrift.

The starting compounds of the formula (10) are known from the literature or they can be obtained by methods similar to those employed for obtaining the known compounds. Among the starting materials of the formula (9), the compound in which $R_2=R_1'''=$ phenyl is known from Beilsteins Handbuch der organischen Chemie, Vol. 24, page 472 or from Chemical Abstracts, Vol. 51, 930 h, and the correspondingly substituted barbituric acids of the formula (9) can be obtained by methods similar to the procedures described therein (cf. in this connection also the particulars given in the preparatory Examples herein).

The invention is illustrated by the following Examples, in which the parts and percentages are by weight unless otherwise stated.

(a) Preparatory Examples

Example 1

To a solution of 15.6 g of 1,3-dimethylbarbituric acid in 150 ml of dimethyl sulfoxide are added dropwise 10.1 g of triethylamine at a temperature of 20° to 30° C. and with continual stirring, and thereafter 15.6 g of 4-chlorophenylisocyanate, dissolved in a small amount of dimethyl sulfoxide. The reaction mixture is stirred for a further 24 hours at room temperature and then poured into a solution of 15 ml of conc. hydrochloric acid in 350 ml of water. The resultant condensation product is collected with suction and recrystallised from dioxane, affording the compound of the formula

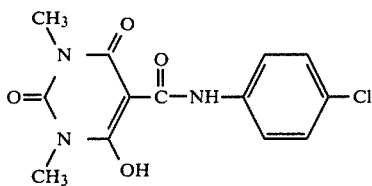

(101)

with a melting point of 225°–227° C.

The following compounds of the formula (A) listed in Table 1 are obtained in analogous manner:

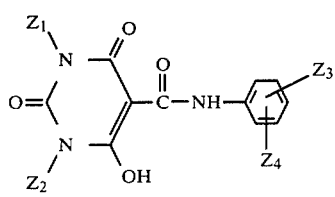

(A)

TABLE 1

| Compound No. | $Z_1$ | $Z_2$ | $Z_3$ | $Z_4$ | Melting point (°C.) |
|---|---|---|---|---|---|
| 102 | CH$_3$ | CH$_3$ | 2-Cl | 4-Cl | 208–210 |
| 103 | CH$_3$ | CH$_3$ | 3-CF$_3$ | 4-Cl | 180–182 |
| 104 | CH$_3$ | CH$_3$ | 4-CF$_3$ | H | 188–190 |
| 105 | CH$_3$ | CH$_3$ | 3-CF$_3$ | H | 139–141 |
| 106 | CH$_3$ | CH$_3$ | 3-CF$_3$ | 5-CF$_3$ | 184–185 |
| 107 | CH$_3$ | CH$_3$ | 4-Br | H | 243–245 |
| 108 | CH$_3$ | CH$_3$ | 4-J | H | 254–255 |
| 109 | CH$_3$ | CH$_3$ | 4-F | H | 188–190 |
| 110 | CH$_3$ | CH$_3$ | 3-Cl | 4-Cl | 205–206 |
| 111 | CH$_3$ | CH$_3$ | 4-Cl | 2-CH$_3$ | 179–180 |
| 112 | CH$_3$ | CH$_3$ | 2-Cl | 5-CF$_3$ | 212–213 |
| 113 | CH$_3$ | CH$_3$ | 3-Cl | 4-CF$_3$ | 160–161 |
| 114 | CH$_3$ | C$_2$H$_5$ | 3-CF$_3$ | 4-Cl | 124–126 |
| 115 | CH$_3$ | C$_2$H$_5$ | 4-Br | H | 193–195 |
| 116 | CH$_3$ | C$_2$H$_5$ | 2-Cl | 4-Cl | 133–135 |
| 117 | CH$_3$ | C$_2$H$_5$ | 3-CF$_3$ | H | 116–118 |
| 118 | CH$_3$ | (i)-C$_3$H$_7$ | 4-Cl | H | 183–185 |
| 119 | CH$_3$ | (i)-C$_3$H$_7$ | 2-Cl | 4-Cl | 163–166 |
| 120 | CH$_3$ | (i)-C$_3$H$_7$ | 4-Br | H | 183–185 |
| 121 | CH$_3$ | (i)-C$_4$H$_9$ | 4-Br | H | 156–157 |
| 122 | CH$_3$ | (i)-C$_4$H$_9$ | 2-Cl | 4-Cl | 157–158 |
| 123 | CH$_3$ | (i)-C$_4$H$_9$ | 3-CF$_3$ | H | 100–102 |
| 124 | CH$_3$ | (i)-C$_4$H$_9$ | 4-CF$_3$ | H | 115–117 |
| 125 | CH$_3$ | CH$_2$=CH—CH$_2$— | 4-Br | H | 124–125 |
| 126 | CH$_3$ | CH$_2$=CH—CH$_2$— | 2-Cl | 4-Cl | 143–145 |
| 127 | CH$_3$ | CH$_2$=CH—CH$_2$— | 3-CF$_3$ | H | 106–108 |
| 128 | CH$_3$ | CH$_2$=CH—CH$_2$— | 4-CF$_3$ | H | 109–111 |
| 129 | CH$_3$ | CH$_3$ | 3-Cl | 5-Cl | |
| 130 | CH$_3$ | C$_2$H$_5$ | 4-Cl | H | |
| 131 | C$_2$H$_5$ | (i)-C$_3$H$_7$ | 4-Cl | H | |
| 132 | CH$_3$ | CH$_2$=CH—CH$_2$— | 4-Cl | H | |
| 133 | C$_2$H$_5$ | C$_2$H$_5$ | 3-Cl | 4-Cl | |
| 134 | C$_2$H$_5$ | C$_2$H$_5$ | 3-CF$_3$ | 4-Cl | |
| 135 | C$_2$H$_5$ | C$_2$H$_5$ | 4-Cl | H | 164–166 |
| 136 | C$_2$H$_5$ | C$_2$H$_5$ | 2-Cl | 4-Cl | 143–144 |
| 137 | C$_2$H$_5$ | C$_2$H$_5$ | 4-Br | H | 170–172 |
| 138 | C$_2$H$_5$ | C$_2$H$_5$ | 4-CF$_3$ | H | |
| 139 | C$_2$H$_5$ | C$_2$H$_5$ | 3-CF$_3$ | 5-CF$_3$ | |
| 140 | C$_2$H$_5$ | C$_2$H$_5$ | 3-Cl | 4-CF$_3$ | |
| 141 | C$_2$H$_5$ | C$_2$H$_5$ | 3-CF$_3$ | H | |
| 142 | C$_2$H$_5$ | C$_2$H$_5$ | 3-Cl | 5-Cl | |

The two compounds of the formula

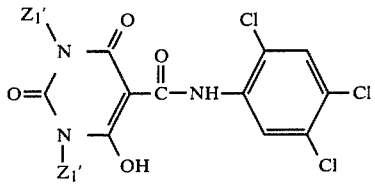

wherein $Z_1'$ is CH$_3$ or C$_2$H$_5$ are obtained in analogous manner.

Example 2

8.6 g (0.05 mole) of 1,3-dimethyl-2-thiobarbituric acid are dissolved in 200 ml of benzene and 5.0 g (0.05 mole) of triethylamine are added at room temperature. The solution is warmed to 35°–40° C. and then 7.7 g (0.05 mole) of 4-chlorophenylisocyanate are slowly added dropwise with stirring and reflux cooling. The reaction mixture is heated under reflux for 15 hours, then cooled and acidified with 10 ml of concentrated hydrochloric acid. The solvent is distilled off in vacuo. The residue is taken up in 200 ml of water, whereupon triethylammonium chloride dissolves. The solid is collected by filtration, washed with two 50 ml portions of methanol and dried, affording 13.5 g (83% of theory) of the compound of the formula

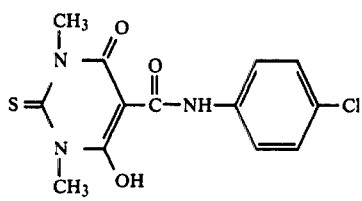

(201)

with a melting point of 243°–245° C.

The following compounds of the formula (B) listed in Table 2 are obtained in analogous manner:

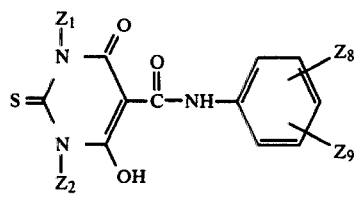

(B)

TABLE 2

| Compound No. | $Z_1$ | $Z_2$ | $Z_8$ | $Z_9$ | Melting point (°C.) |
|---|---|---|---|---|---|
| 202 | $CH_3$ | $CH_3$ | 4-Cl | H | |
| 203 | $CH_3$ | $CH_3$ | 4-Br | H | |
| 204 | $CH_3$ | $CH_3$ | 4-$CF_3$ | H | |
| 205 | $CH_3$ | $CH_3$ | 4-Cl | 3-Cl | |
| 206 | $CH_3$ | $CH_3$ | 4-Cl | 2-Cl | |
| 207 | $CH_3$ | $CH_3$ | 4-Cl | 3-$CF_3$ | |
| 208 | $CH_3$ | $CH_3$ | 4-$CF_3$ | 3-Cl | 185 |
| 209 | $CH_3$ | $CH_3$ | 3-$CF_3$ | H | |
| 210 | $CH_3$ | $CH_3$ | 3-$CF_3$ | 5-$CF_3$ | |
| 211 | $CH_3$ | $CH_3$ | 3-Cl | 5-Cl | |
| 212 | $C_2H_5$ | $C_2H_5$ | 4-Cl | H | |
| 213 | $C_2H_5$ | $C_2H_5$ | 4-Br | H | |
| 214 | $C_2H_5$ | $C_2H_5$ | 4-$CF_3$ | H | 162–165 (triethyl-ammonium salt) |
| 215 | $C_2H_5$ | $C_2H_5$ | 4-Cl | 3-Cl | |
| 216 | $C_2H_5$ | $C_2H_5$ | 4-Cl | 2-Cl | |
| 217 | $C_2H_5$ | $C_2H_5$ | 4-Cl | 3-$CF_3$ | |
| 218 | $C_2H_5$ | $C_2H_5$ | 4-$Cf_3$ | 3-Cl | |
| 219 | $C_2H_5$ | $C_2H_5$ | 3-$CF_3$ | H | |
| 220 | $C_2H_5$ | $C_2H_5$ | 3-$CF_3$ | 5-$CF_3$ | |
| 221 | $C_2H_5$ | $C_2H_5$ | 3-Cl | 5-Cl | |
| 222 | $CH_3$ | $C_2H_5$ | 4-Cl | H | |
| 223 | $CH_3$ | $C_2H_5$ | 4-Br | H | |
| 224 | $CH_3$ | $C_2H_5$ | 4-$CF_3$ | H | |
| 225 | $CH_3$ | $C_2H_5$ | 4-Cl | 3-$CF_3$ | |
| 226 | $CH_3$ | $i$-$C_3H_7$ | 4-Cl | H | |
| 227 | $CH_3$ | $i$-$C_3H_7$ | 4-Br | H | |
| 228 | $CH_3$ | $i$-$C_3H_7$ | 4-$CF_3$ | H | |
| 229 | $CH_3$ | $i$-$C_3H_7$ | 4-Cl | 3-$CF_3$ | |
| 230 | $C_2H_5$ | $i$-$C_3H_7$ | 4-Cl | H | |
| 231 | $C_2H_5$ | $i$-$C_3H_7$ | 4-Br | H | |
| 232 | $C_2H_5$ | $i$-$C_3H_7$ | 4-$CF_3$ | H | |
| 233 | $C_2H_5$ | $i$-$C_3H_7$ | 4-Cl | 3-$CF_3$ | |
| 234 | $CH_3$ | $CH_3$ | 4-$NO_2$ | 3-Cl | 224–225 |
| 235 | $CH_3$ | $CH_3$ | 4-Cl | 2-$CH_3$ | 206–207 |
| 236 | $CH_3$ | $C_2H_5$ | 4-Cl | 3-Cl | 150–154 |

Example 3

With constant stirring, 2.1 g of triethylamine and then a solution of 3.2 g of 4-chlorophenylisocyanate in 50 ml of dimethyl sulfoxide are added dropwise at a temperature of 20°–25° C. to a solution of 5.6 g of 1,3-diphenyl-barbituric acid in 50 ml of dimethyl sulfoxide. The temperature is then raised to 40° C. and the reaction mixture is stirred for a further 24 hours at this temperature and then poured into a solution of 10 ml of conc. hydrochloric acid in 200 ml of water. The resultant precipitate is collected by suction, washed with water and dried in vacuo, affording 5.8 g (66.8% of theory) of reddish crystals with a melting point of 188°–190° C. Recrystallisation of the crude product from xylene (mixture of isomers) and then from ethanol yields the compound of the formula

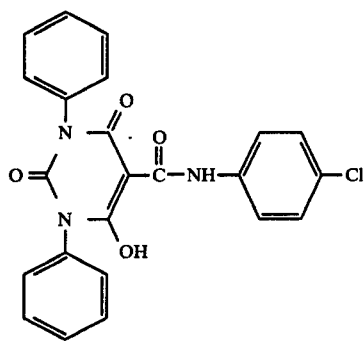

(301)

in the form of colourless needles with a melting point of 218°–219° C. The compounds of the formula (C) listed in Table 3 are obtained in analogous manner:

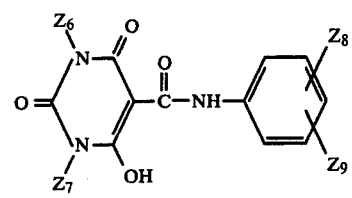

(C)

TABLE 3

| Compound No. | $Z_6$ | $Z_7$ | $Z_8$ | $Z_9$ | Melting point (°C.) |
|---|---|---|---|---|---|
| 302 | –C₆H₅ | –C₆H₅ | 3-$CF_3$ | H | 174–175 |
| 303 | –C₆H₄–Cl | –C₆H₄–Cl | H | 4-Cl | 229–230 |
| 304 | –C₆H₄–Cl | –C₆H₄–Cl | 3-Cl | 4-Cl | 250–252 |
| 305 | –C₆H₄–Cl | –C₆H₄–Cl | 3-$CF_3$ | H | 178–179 |
| 306 | 2-$CF_3$,-Cl-C₆H₃ | 2-$CF_3$,-Cl-C₆H₃ | 3-Cl | 4-Cl | 238–239 |
| 307 | 3-Cl-C₆H₄– | $CH_3$ | 4-Cl | H | 193–194 |
| 308 | 3-Cl-C₆H₄– | $CH_3$ | 3-Cl | 4-Cl | 190–191 |
| 309 | 3-Cl-C₆H₄– | $CH_3$ | 3-$CF_3$ | H | 171–172 |
| 310 | 4-Cl-C₆H₄– | $CH_3$ | 4-Cl | H | 220–221 |

The 1,3-diphenylbarbituric acid required as starting material for obtaining compounds (301) and (302) is known (e.g. Beilstein, Vol. 24, page 472 or Chemical Abstracts, Vol. 51, 930 h) and has a melting point of 244°–245° C.

The 1-(3-chlorophenyl)-3-methylbarbituric acid required as starting material for obtaining compounds (307) to (309) is known from German Offenlegungsschrift 2 509 560. 1-(4-Chlorophenyl)-3-methylbarbituric acid [starting material for compound (301)] can be obtained in analogous manner.

The starting material for obtaining compounds (303) to (305), 1,3-di-(4-chlorophenyl)-barbituric acid, is prepared as follows.

With constant stirring, a solution of 33.9 g of malonyl dichloride (content ~95%) in 30 ml of ethylene chloride is added dropwise to a suspension of 42.2 g of N,N'-bis-(4-chlorophenyl)urea in 200 ml of ethylene chloride. The temperature is raised in the course of 30 minutes to 75°–85° C., whereupon dehydrochlorination occurs. The reaction mixture is stirred at this temperature for a further 8 hours, filtered hot, and the filtrate is freed from solvent by rotary evaporation. The residual oil, which gradually solidifies, is treated with petroleum ether (b.p. 35°–70° C.), collected by suction and dried. Two recrystallisations from xylene (mixture of isomers)/ethanol (10:1) yields 20.3 g (38.8% of theory, based on urea derivative) of the compound of the formula

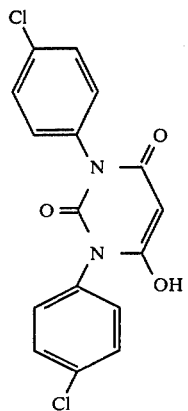

with a melting point of 178°–180° C. (with decomposition).

1,3-Di-(3-trifluoromethyl-4-chlorophenyl)barbituric acid [starting material for obtaining compound (306)] is obtained in analogous manner from N,N'-bis-(3-trifluoromethyl-4-chlorophenyl)urea and malonyl dichloride.

The substituted isocyanates likewise required as starting materials are known from the literature or they can be obtained by methods analogous to those employed for obtaining the known compounds. The compounds of formula (C) above listed in Table 4 are obtained in analogous manner:

TABLE 4

| Compound No. | $Z_6$ | $Z_7$ | $Z_8$ | $Z_9$ |
|---|---|---|---|---|
| 311 | $C_6H_5$ | $C_6H_5$ | 3-Cl | 4-Cl |
| 312 | $C_6H_5$ | $C_6H_5$ | 4-Cl | 2-Cl |
| 313 | m-$ClC_6H_4$ | $CH_3$ | 4-Br | H |
| 314 | m-$ClC_6H_4$ | $CH_3$ | 4-Cl | 2-Cl |
| 315 | p-$ClC_6H_4$ | $CH_3$ | 4-Br | H |

TABLE 4-continued

| Compound No. | $Z_6$ | $Z_7$ | $Z_8$ | $Z_9$ |
|---|---|---|---|---|
| 316 | p-$ClC_6H_4$ | $CH_3$ | 4-$CF_3$ | H |
| 317 | p-$ClC_6H_4$ | $CH_3$ | 4-Cl | 3-Cl |
| 318 | p-$ClC_6H_4$ | $CH_3$ | 4-Cl | 2-Cl |

(b) The following Examples 4 to 7 will serve to illustrate the method of the invention in more detail.

Example 4

A 0.4% stock solution of each of the compounds of the formulae (101) to (142), (201) to (236) and (301) to (318), in ethylene glycol monomethyl ether is prepared. Then an aqueous treatment bath containing, in 120 ml of distilled water, 0.12 ml of a wetting agent and dispersant, 0.6 ml of formic acid 1:10 and 0.75 ml of the respective 0.4% stock solution, is prepared at room temperature. Then 3 g of wool flannel are wetted with hot water and put into the bath at room temperature. While constantly circulating the wook sample, the bath temperature is raised to 60° C. in the course of 20 minutes and treatment is carried out for 30 minutes at 60° C. The bath is then cooled, the wool sample rinsed twice for 3 minutes with distilled water, squeezed out by hand and dried in the air. The active ingredient concentration is 1000 ppm, based on the weight of the wool.

The dried sample is subjected to the mothproofing test (protection against feeding damage caused by the webbing clothes moth *Tineola biselliella Hum.*), in accordance with SNV 195901, and to the resistance test against larvae of the fur beetle (*Attagenus piceus OL.*) and carpet bettle (*Anthrenus vorax Wat.*) in accordance with SNV 195902. In these tests, larvae of Anthrenus vorax and 6- to 7-week-old larvae of Attagenus piceus are used. Pieces of the same size are cut out of the treated wool samples and subjected for 14 days at constant temperature (28° C.) and constant relative humidity (65%) to attack (feeding) by 15 larvae of each of the pests. Evaluation is made on the one hand according to the relative loss in weight of the test sample and, on the other, according to the number of still living organisms.

The tested compounds are very effective against the three pests, especially against the beetle larvae.

Example 5

A 0.4% stock solution of each of the compounds of the formulae (101) to (142), (201) to (236) and (301) to (318), in ethylene glycol monomethyl ether is prepared. Each of the stock solutions (12.5 ml) is diluted to 50 ml (solution 1) with ethylene glycol monomethyl ether which contains 0.65 g/l of a wetting agent and dispersant. Solution 1 (25 ml) is then diluted to 50 ml (solution 2) with ethylene glycol monomethyl ether which contains 0.5 g/l of a wetting agent and dispersant. Solution 2 (25 ml) is diluted in turn to 50 ml (solution 3) with ethylene glycol monomethyl ether which contains 0.5 g/l of a wetting agent and dispersant.

3 ml of each of solutions 1, 2 and 3 are poured into crystallisation dishes and a disc of wool flannel is wetted for 3 seconds therein. The moist discs are then padded between aluminium sheets to a pick-up of 50% of each solution. The concentrations of active ingredient are, respectively, 500 ppm, 250 ppm and 125 ppm for the discs treated with solutions 1, 2 and 3. The discs are then dried in the air and subjected to the same biological tests as in Example 4.

The tested compounds are very effective against all 3 pests, especially against the beetle larvae.

Example 6

A 10% solution of each of the compounds, of the formulae (103), (107), (113), (301) and (302) in ethylene glycol monomethyl ether is prepared. One part by volume of each solution is diluted with 200 parts by volume of a solvent suitable for dry cleaning, for example a suitable petroleum fraction or perchloroethylene. If desired, other cleaning promoters can be added. Woollen articles are then treated in the conventional manner in this cleaning fluid and subsequently centrifuged to a solvent pick-up of about 100% of the weight of the wool. After drying, the articles have a good protective finish against pests that feed on keratin, especially against beetles.

A protective finish against moths and especially beetles is also obtained by substituting the other compounds of Examples 1 to 3 for the compounds of the formulae (103), (107), (113), (301) and (302) and repeating the above procedure.

Similar mixtures can also be used for spraying or sprinkling wool in any state of processing.

Example 7

A 0.5% solution of each of the active compounds of the formulae (101) to (142), (201) to (236) and (301) in methylene chloride, trichloroethylene or a low boiling petroleum fraction is prepared. A woollen article is sprayed with each solution from a conventional spray device, so that 2×15 g/m² of active ingredient solution is applied, corresponding to a concentration of about 400 ppm on the material at a 30% consumption of the aerosol. The treated woollen fabric has a good protective finish against moths and especially against beetles.

Example 8

A 0.4% stock solution of a 1:1 mixture of the compounds of the formula (102) and the pyrethroid of the formula

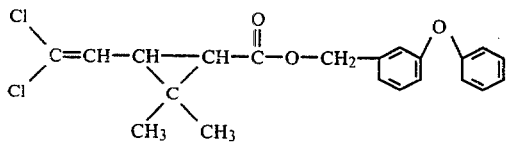

in ethylene glycol monomethyl ether is prepared. Then aqueous treatment baths containing, in 120 ml of distilled water, 0.12 ml of a wetting agent and dispersant, 0.6 ml of formic acid 1:10 and 0.2 ml, 0.1 ml and 0.05 ml respectively of the 0.4% stock solution, are prepared at room temperature. Then 3 g of wool flannels are wetted with hot water and put into the baths at room temperature. While constantly circulating the wool samples, the bath temperature is raised to 60° C. in the course of 20 minutes and treatment is carried out for 30 minutes at 60° C. The baths are then cooled, the wool samples rinsed twice for 3 minutes with distilled water, squeezed out by hand and dried in the air. The active ingredient concentration is 250, 125 and 60 ppm respectively, based on the weight of the wool.

The dried samples are subjected to the mothproofing test (protection against feeding damage caused by the webbing clothes moth *Tineola biselliella Hum.*), in accordance with SNV 195901, and to the resistance test against larvae of the fur beetle (*Attagenus piceus OL.*) and carpet beetle *(Anthrenus vorax Wat.)* in accordance with SNV 195902. In these tests, larvae of Anthrenus vorax and 6- to 7-week-old larvae of *Attagenus piceus* are used. Pieces of the same size are cut out of the treated wool samples and subjected for 14 days at constant temperature (28° C.) and constant relative humidity (65%) to attack (feeding) by 15 larvae of each of the pests. Evaluation is made on the one hand according to the relative loss in weight of the test sample and, on the other, according to the number of still living organisms.

The tested mixture is most effective against all 3 pests at all concentrations employed.

A fabric provided with a complete moth- and beetle-proof finish is obtained by using a 1:1 mixture of the compound of the formula (102) and the pyrethroid of the formula

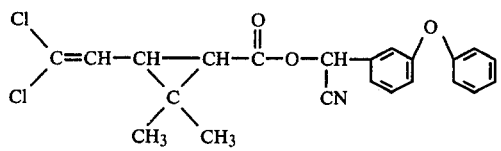

and repeating the above procedure.

EXAMPLE 9

Protective finishes against moths and beetles similar as the finishes obtained in Example 8 can also be obtained by using other mixtures of 5-phenylcarbamoyl-barbituric acid derivatives with compounds which are effective against insects that feed on keratin, especially moths. The substrates are impregnated, and the activity of such mixtures are tested, in accordance with the procedure described in Example 8. It may on occasion be necessary or advantageous to employ higher concentrations of the respective mixture, e.g. up to 1000 ppm. As one component it is also possible to use the compound of the formula (102), likewise aslo one or more of the compounds of the formulae (101), (103) to (142), (201) to (236) and/or (301) to (318).

As second component, one or more of the following compounds is used:

(a) Pyrethroid and phenylacetic compounds of the formulae:

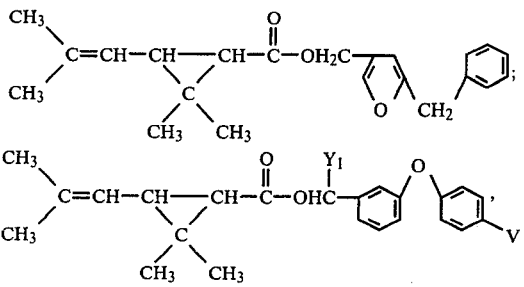

wherein
V=H, Cl, Br, F, CH₃ or NO₂ and
Y₁=H, CN, CH₃, C₂H₅, i—C₃H₇,

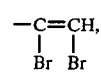

—C≡CH, —C≡C—CH₃, —CH=CH₂, —CH=CH—CH₃, —CH₂—CH=CH₂ or —CH₂—CH=CHCl;

[Structure: H₃C\C=CH—CH—CH—C(=O)—O—HC(Y₁)—phenyl—O—pyridyl, with C(CH₃)(CH₃) bridge]

wherein
Y₁ = H, CN or CH₃;

[Structure: (H₃C)₂C=CH—CH—CH—C(=O)—O—CH(Y₁)—phenyl—O—phenyl, with C(CH₃)(CH₃)]

wherein
Y₁ = H, CN or —C≡CH;

[Structure: Cl₂C=CH—CH—CH—C(=O)—O—CH(Y₁)—phenyl—O—phenyl—V, with C(CH₃)(CH₃)]

wherein
V = H, Cl, Br, F, CH₃ or NO₂ and
Y₁ = H, CN, CH₃, C₂H₅, i—C₃H₇, $-C(Br)=CHBr$, —C≡CH, —C≡C—CH₃, —CH=CH₂, —CH=CH—CH₃, —CH₂—CH=CH₂, —CH₂—CH=CHCl or —C≡C—C₆H₅;

[Structure: Br₂C=CH—CH—CH—C(=O)—O—CH(Y₁)—phenyl—O—phenyl—V, with C(CH₃)(CH₃)]

wherein
V = H, Cl, Br, F, CH₃ or NO₂ and
Y₁ = H, CN, CH₃, C₂H₅, i—C₃H₇, $-C(Br)=CHBr$, —C≡CH, —C≡C—CH₃, —C=CH₂, —CH=CH—CH₃, —CH₂—CH=CH₂, —CH₂—CH=CHCl or —C≡C—C₆H₅;

[Structure: F₂C=CH—CH—CH—C(=O)—O—CH(Y₁)—phenyl—O—phenyl—V, with C(CH₃)(CH₃)]

wherein
V = H, Cl, Br, F, CH₃ or NO₂ and
Y₁ = H, CN, CH₃, C₂H₅, i—C₃H₇, $-C(Br)=CHBr$, —C≡CH, —C≡C—CH₃, —CH=CH₂, —CH=CH—CH₃, —CH₂—CH=CH₂, —CH₂—CH=CHCl or —C≡C—C₆H₅;

[Structure: Cl₂C=CH—CH—CH—C(=O)—O—CH(CN)—phenyl—O—phenyl—CF₃, with C(CH₃)(CH₃)]

[Structure: Cl₂C=CH—CH—CH—C(=O)—O—CH(Y₁)—phenyl—O—pyridyl, with C(CH₃)(CH₃)]

wherein
Y₁ = H, CN or CH₃;

[Structure: Cl₂C=CH—CH—CH—C(=O)—O—CH(Y₁)—phenyl—O—V₁, with C(CH₃)(CH₃)]

wherein
Y₁ = H, CN or CH₃ and
V₁ = CH₂—CH=CH₂, —CH₂—C≡CH, —CH₂—CH=CH—CH₃,

—CH₂—phenyl, —CH=C(Cl)₂, —C(F)=C(F)(Cl) or —C(F)=CF₂;

[Structure: Br₂C=C—CH—CH—C(=O)—O—CH(CN)—phenyl—O—phenyl, with C(CH₃)(CH₃) and Br substituent]

[Structure: Cl₂C=CH—CH—CH—C(=O)—O—CH(C≡C—CH₃)—C(Br)=CH—phenyl, with C(CH₃)(CH₃)]

[Structure: F₂C=CH—CH—CH—C(=O)—O—CH₂—CH=C(Cl)—CH₂—phenyl, with C(CH₃)(CH₃)]

[Structure: phenyl—CH=CH—CH—CH—C(=O)—O—CH₂—(furan)—CH₂—phenyl, with C(CH₃)(CH₃)]

-continued

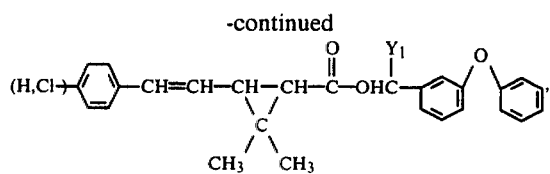

wherein
$Y_1$ = H, CN, CH$_3$, C$_2$H$_5$, i—C$_3$H$_7$,

—C≡CH, —C≡C—CH$_3$, —CH=CH$_2$, —CH=CH—CH$_3$, —CH$_2$—CH=CH$_2$ or —CH$_2$—CH=CHCl;

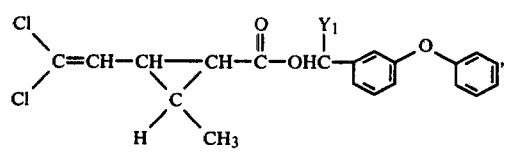

wherein
$Y_1$ = H, CN, CH$_3$, C$_2$H$_5$, i—C$_3$H$_7$,

—C≡CH, —C≡C—CH$_3$, —CH=CH—CH$_3$, —CH$_2$—CH=CH$_2$ or —CH$_2$—CH=CHCl;

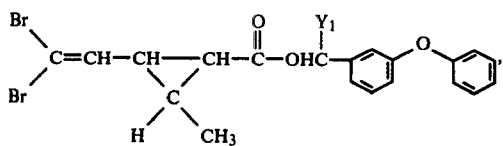

wherein
$Y_1$ = H, CN, CH$_3$, C$_2$H$_5$, i—C$_3$H$_7$,

—C≡CH, —C≡C—CH$_3$, —CH=CH$_2$, —CH=CH—CH$_3$, —CH$_2$—CH=CH$_2$ or —CH$_2$—CH=CHCl;

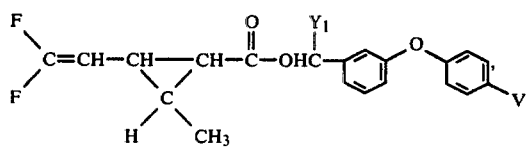

wherein
$Y_1$ = H, CN, CH$_3$, C$_2$H$_5$, i—C$_3$H$_7$,

—C≡CH, —C≡C—CH$_3$, —CH=CH$_2$, —CH=CH—CH$_3$, —CH$_2$—CH=CH$_2$ or —CH$_2$—CH=CHCl;

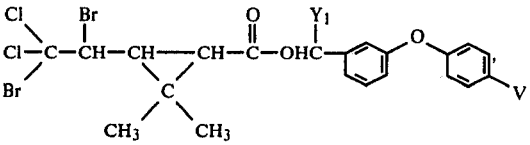

wherein
V = H, Cl, Br, F, CH$_3$ or NO$_2$ and
$Y_1$ = H, CN, CH$_3$, C$_2$H$_5$, i—C$_3$H$_7$,

—C≡CH, —C≡C—CH$_3$, —CH=CH$_2$, —CH=CH—CH$_3$, —CH$_2$—CH=CH$_2$ or —CH$_2$—CH=CHCl;

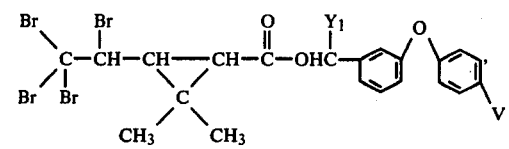

wherein
V = H, Cl, Br, F, CH$_3$ or NO$_2$ and
$Y_1$ = H, CN, CH$_3$, C$_2$H$_5$, i—C$_3$H$_7$,

—C≡CH, —C≡C—CH$_3$, —CH=CH—CH$_3$, —CH$_2$—CH=CH$_2$ or —CH$_2$—CH=CHCl;

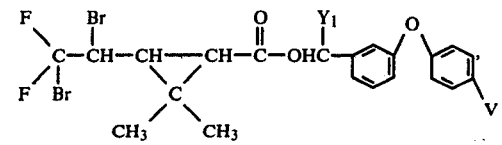

wherein
V = H, Cl, Br, F, CH$_3$ or NO$_2$ and
$Y_1$ = H, CN, CH$_3$, C$_2$H$_5$, i—C$_3$H$_7$,

—C≡CH, —C≡C—CH$_3$, —CH=CH—CH$_3$, —CH$_2$—CH=CH$_2$ or —CH$_2$—CH=CHCl;

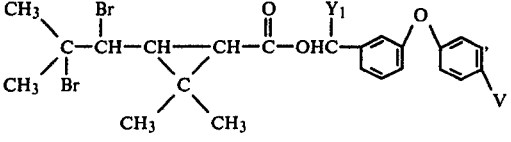

wherein
V = H, Cl, Br, F, CH$_3$ or NO$_2$ and
$Y_1$ = H, CN, CH$_3$, C$_2$H$_5$, i—C$_3$H$_7$,

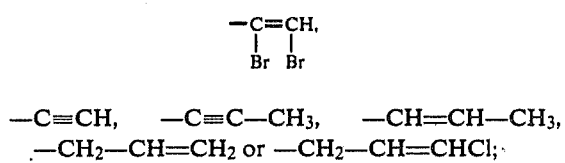
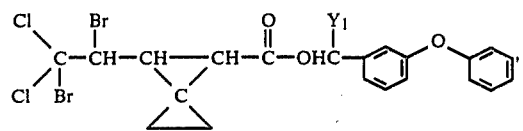
wherein
$Y_1$ = H or CN;
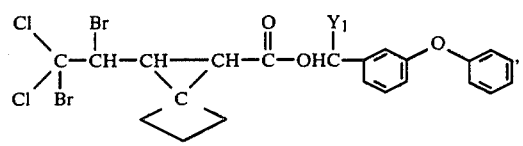
wherein
$Y_1$ = H or CN;
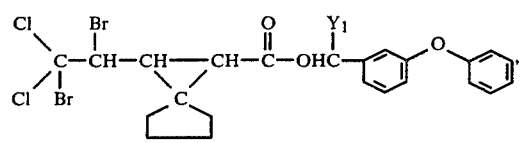
wherein
$Y_1$ = H or CN;
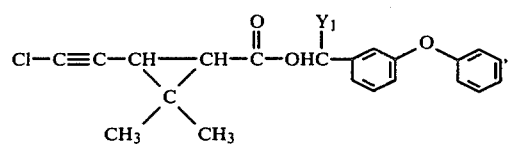
wherein
$Y_1$ = H, CN or —CH=CH—CH$_3$;
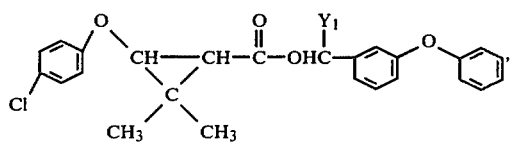
wherein
$Y_1$ = H or CN;
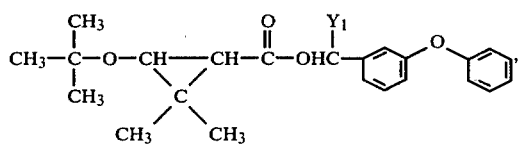
wherein
$Y_1$ = H or CN;
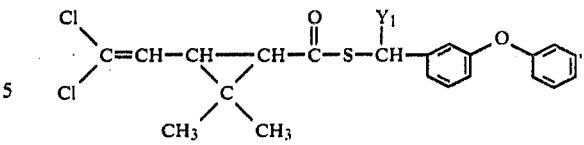
wherein
$Y_1$ = H, CH$_3$ or CN;
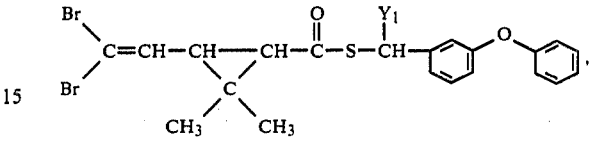
wherein
$Y_1$ = H or CH$_3$;
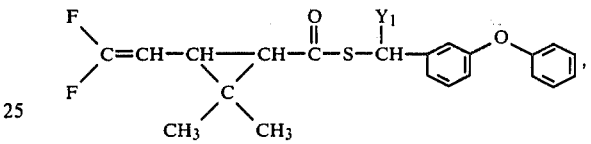
wherein
Y = H or CH$_3$;
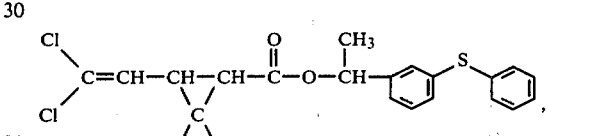
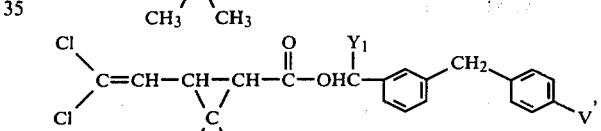
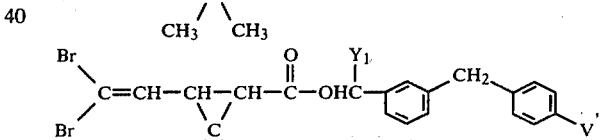
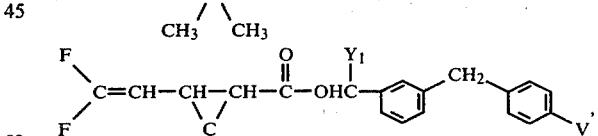
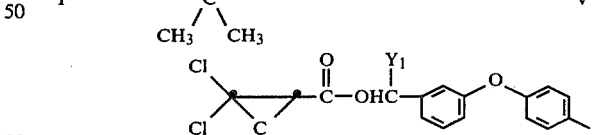
wherein
V = H, Cl, Br, F, CH$_3$ or NO$_2$ and
$Y_1$ = H, CN, CH$_3$, C$_2$H$_5$, i—C$_3$H$_7$,
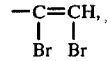
—C≡CH, —C≡C—CH$_3$, —CH=CH$_2$, —CH=CH—CH$_3$, —CH$_2$—CH=CH$_2$, —CH$_2$—CH=CHCl or —C≡C—C$_6$H$_5$;

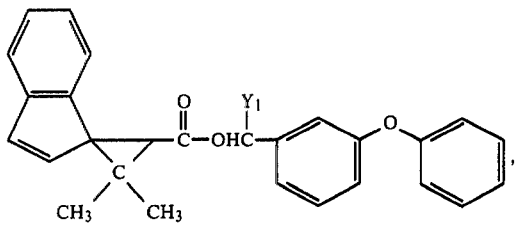

wherein
$Y_1$ = H, CN, CH$_3$ or —C≡C—CH$_3$;

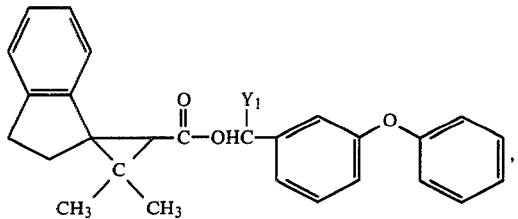

wherein
$Y_1$ = H, CN, CH$_3$ or —C≡C—CH$_3$;

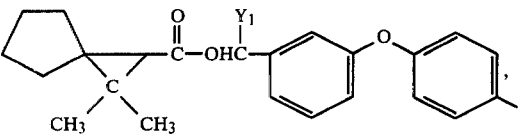

wherein
$Y_1$ = H, CN, CH$_3$ or —C≡C—CH$_3$;

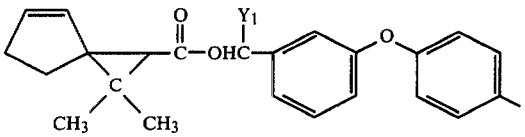

wherein
$Y_1$ = H, CN, CH$_3$ or —C≡C—CH$_3$;

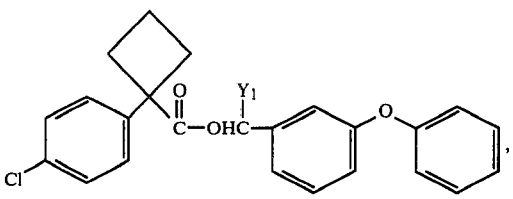

wherein
$Y_1$ = H, CN or —C≡CH;

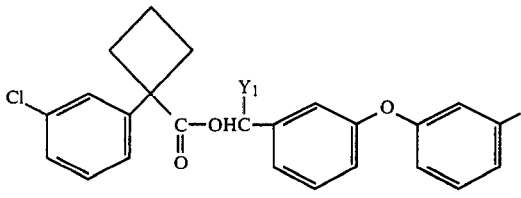

wherein
$Y_1$ = H or CN;

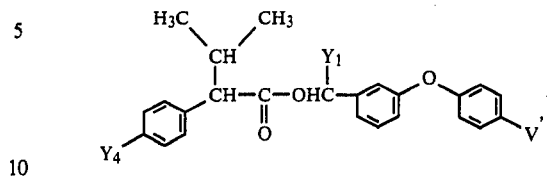

wherein
V = H, Cl, Br, F, CH$_3$ or NO$_2$ and
$Y_1$ = H, CN, CH$_3$, C$_2$H$_5$, i—C$_3$H$_7$, $$-\underset{Br}{C}=\underset{Br}{CH},$$

—C≡CH, —C≡C—CH$_3$, —CH=CH—CH$_3$, —CH$_2$—CH=CH$_2$, —CH$_2$—CH=CHCl or —C≡C—C$_6$H$_5$ and
$Y_4$ = H, CH$_3$, Cl, NO$_2$, CN, —OCH$_3$, $$-O-CH\begin{smallmatrix}CH_3\\CH_3\end{smallmatrix},$$

—O—CH$_2$—C≡CH or —O—CH$_2$—CH=CH$_2$;

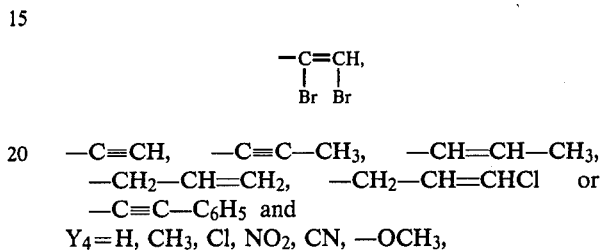

wherein
V = H, Cl, Br, F, CH$_3$ or NO$_2$ and
$Y_1$ = H, CN, CH$_3$, C$_2$H$_5$, i—C$_3$H$_7$, $$-\underset{Br}{C}=\underset{Br}{CH},$$

—C≡CH, —C≡C—CH$_3$, —CH=CH—CH$_3$, —CH$_2$—CH=CH$_2$ or —CH$_2$—CH=CHCl;

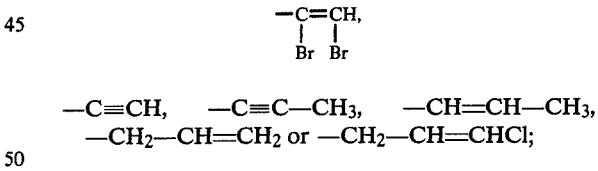

wherein
V = H, Cl, Br, F, CH$_3$ or NO$_2$ and
$Y_1$ = H, CN, CH$_3$, C$_2$H$_5$, i—C$_3$H$_7$, $$-\underset{Br}{C}=\underset{Br}{CH},$$

—C≡CH, —C≡C—CH$_3$, —CH=CH—CH$_3$, —CH$_2$—CH=CH$_2$ or —CH$_2$—CH=CHCl;

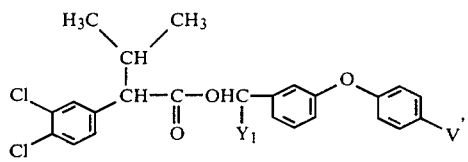

wherein
V = H, Cl, Br, F, CH₃ or NO₂ and
Y₁ = H, CN, CH₃, C₂H₅, i—C₃H₇,

—C≡CH, —C≡C—CH₃, —CH=CH—CH₃,
—CH₂—CH=CH₂ or —CH₂—CH=CHCl;

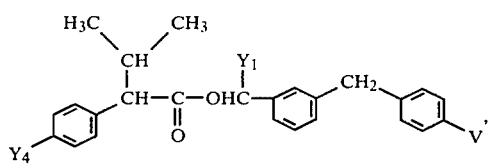

wherein
V = H, Cl, Br, F, CH₃ or NO₂ and
Y₁ = H, CN, CH₃, C₂H₅, i—C₃H₇,

—C≡CH, —C≡C—CH₃, —CH=CH—CH₃,
—CH₂—CH=CH₂ or —CH₂—CH=CHCl; and
Y₄ = H, CH₃, Cl, NO₂, CN, —OCH₃,

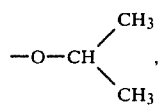

—O—CH₂—C≡CH or —O—CH₂—CH=CH₂;

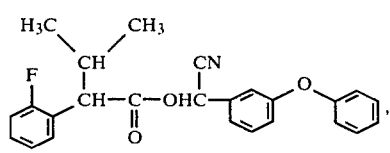

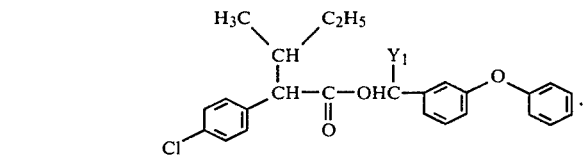

wherein
Y₁ = H or CN;

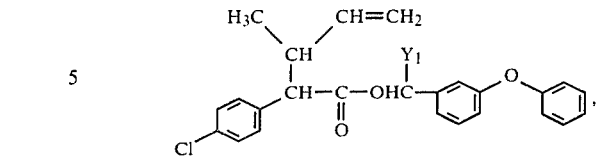

wherein
Y₁ = H or CN;

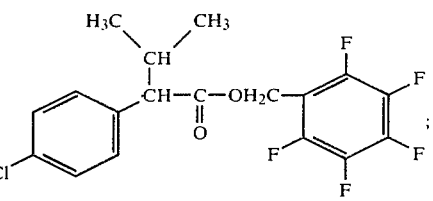

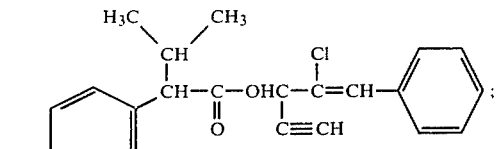

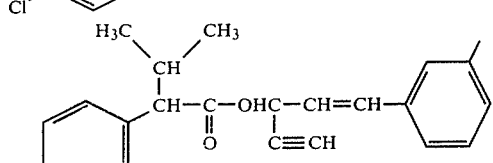

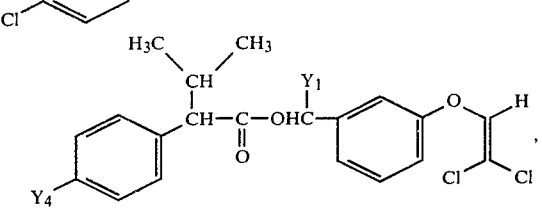

wherein
Y₁ = H, CN or CH₃ and
Y₄ = H or Cl;

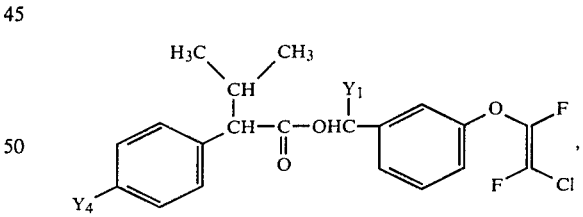

wherein
Y₁ = H, CN or CH₃ and
Y₄ = H or Cl;

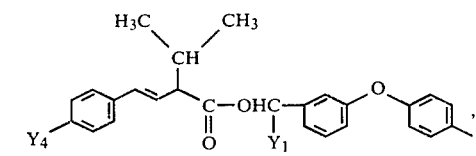

wherein
Y₁ = H, CN or CH₃ and
Y₄ = H or CH₃;

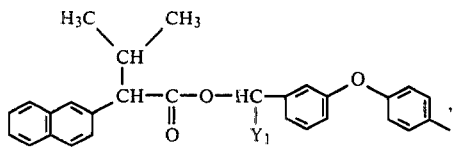

wherein
Y₁ = H or CN;

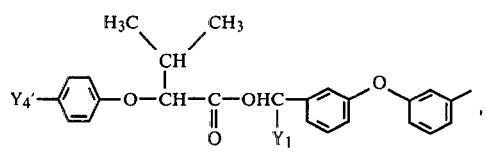

wherein
Y₁ = H or CN and
Y₄' = Cl, CH₃ or H;

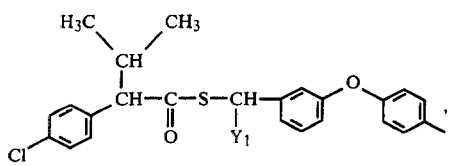

wherein
Y₁ = H, CH₃, —C≡CH or CN;

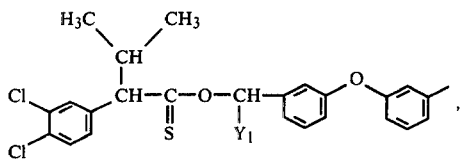

wherein
Y₁ = H or CN;

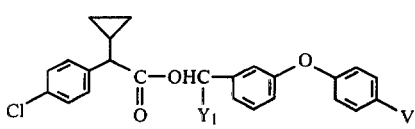

wherein
V = H, Cl, Br, F, CH₃ or NO₂ and
Y₁ = H, CN, CH₃, C₂H₅, i—C₃H₇,

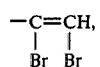

—C≡CH, —C≡C—CH₃, —CH=CH—CH₃,
—CH₂—CH=CH₂ or —CH₂—CH=CHCl;

(b) sulfanilides of the formulae:

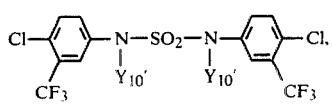

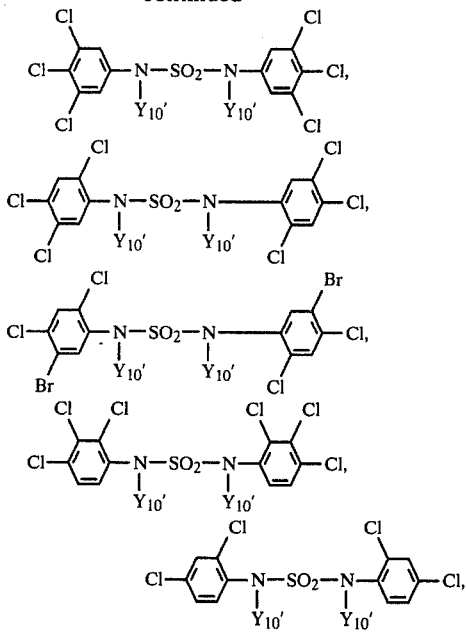

wherein
Y₁₀' = CH₃, C₂H₅, n—C₃H₇, n—C₄H₈, i—C₃H₇ or t—C₄H₉.

All the above compounds, which can advantageously be used in combination with the 5-phenylcarbamoylbarbituric acid compounds to be used in the method of the present invention, are known from the literature or they can be easily obtained by methods analogous to those described therein.

Each mixture can contain several barbituric acid derivatives and/or several pyrethroid, phenylacetic acid or sulfanilide compounds. A mixture of one barbituric acid derivative and one pyrethroid, phenylacetic acid or sulfanilide derivative is, however, preferred. The mixture ratios can vary within wide limits, depending on the requirements; but in actual practice they are between about 4:1 and 1:4, preferably in the range of about 1:1.

What is claimed is:

1. A method of protecting keratinous material from attack by insects that feed on keratin and from feeding damage, which comprises treating said material with compounds of the formula

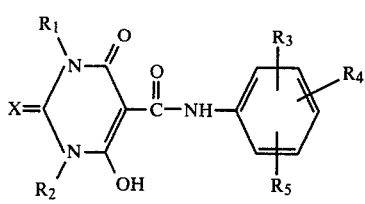

or with tautomeric forms and salts thereof, wherein X is oxygen or sulfur, each of R₁ and R₂ independently is alkyl of 1 to 4 carbon atoms, alkenyl of 3 or 4 carbon atoms, benzyl, phenyl or phenyl substituted by alkyl or alkoxy, each of 1 to 4 carbon atoms, chlorine, bromine, fluorine, nitro or trihalomethyl, but at most 1 nitro and at most 2 trihalomethyl and alkoxy, R₃ is halogen, nitro or trihalomethyl, R₄ is hydrogen, halogen or trihalomethyl, and R₅ is hydrogen, halogen, methyl or methoxy.

2. A method according to claim 1, which comprises treating the material to be protected with compounds of the formula

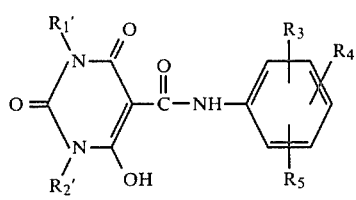

or with the tautomeric forms and salts thereof, wherein each of $R_1'$ and $R_2'$ independently is alkyl of 1 to 4 carbon atoms, alkenyl of 3 or 4 carbon atoms, benzyl or a group of the formula

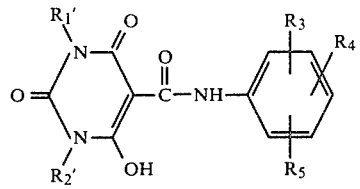

wherein $Z_1$ is hydrogen, chlorine, bromine, fluorine, alkyl or alkoxy, each of 1 to 4 carbon atoms, trihalomethyl or nitro, $Z_2$ is hydrogen, chlorine, bromine, fluorine, alkyl or alkoxy, each of 1 to 4 carbon atoms, or trihalomethyl, $Z_3$ is hydrogen, chlorine, bromine, fluorine or alkyl of 1 to 4 carbon atoms, and $R_3$, $R_4$ and $R_5$ are as defined in claim 1.

3. A method according to claim 1, which comprises treating the material to be protected with compounds of the formula

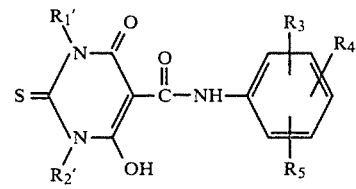

or with the tautomeric forms and salts thereof, wherein each of $R_1'$ and $R_2'$ independently is alkyl of 1 to 4 carbon atoms, alkenyl of 3 or 4 carbon atoms, benzyl or a group of the formula

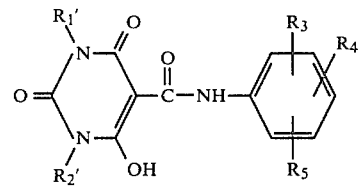

wherein $Z_1$ is hydrogen, chlorine, bromine, fluorine, alkyl or alkoxy, each of 1 to 4 carbon atoms, trihalomethyl or nitro, $Z_2$ is hydrogen, chlorine, bromine, fluorine, alkyl or alkoxy, each of 1 to 4 carbon atoms or trihalomethyl, $Z_3$ is hydrogen, chlorine, bromine, fluorine or alkyl of 1 to 4 carbon atoms; and $R_3$, $R_4$ and $R_5$ are as defined in claim 1.

4. A method according to claim 2, which comprises treating the material to be protected with compounds of the formula

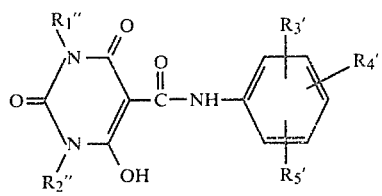

or with the tautomeric forms and salts thereof, wherein each of $R_1''$ and $R_2''$ independently is methyl, ethyl, allyl or a group of the formula

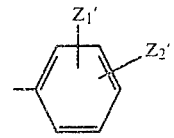

wherein $Z_1'$ is hydrogen, chlorine, bromine, methyl, methoxy, ethoxy, —$CF_3$ or nitro, $Z_2'$ is hydrogen, chlorine, bromine, methyl or —$CF_3$; $R_3'$ is chlorine, bromine or —$CF_3$, $R_4'$ is hydrogen, chlorine or bromine and $R_5'$ is hydrogen, chlorine, bromine, methyl or methoxy.

5. A process according to claim 3, which comprises treating the material to be protected with compounds of the formula

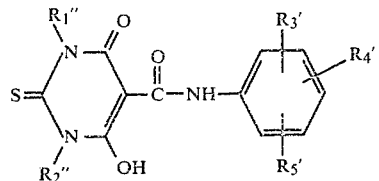

or with the tautomeric forms and salts thereof, wherein each of $R_1''$ and $R_2''$ independently is methyl, ethyl, allyl or a group of the formula

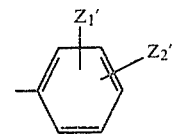

wherein $Z_1'$ is hydrogen, chlorine, bromine, methyl, methoxy, ethoxy, —$CF_3$ or nitro, $Z_2'$ is hydrogen, chlorine, bromine, methyl or —$CF_3$; $R_3'$ is chlorine, bromine or —$CF_3$, $R_4'$ is hydrogen, chlorine or bromine and $R_5'$ is hydrogen, chlorine, bromine, methyl or methoxy.

6. A method according to claim 1, which comprises treating the material to be protected with a mixture of one or more compounds of the formula (1) and a synthetic pyrethroid, an ester or a thioester of an α-alkyl-substituted phenylacetic acid or a substituted sulfanilide.

7. A method according to claim 6, which comprises treating the material to be protected with a mixture of one or more compounds of the formula (1) and a synthetic pyrethroid of the formula

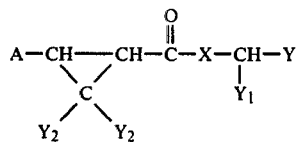

wherein A is Br₂C=CBr—,

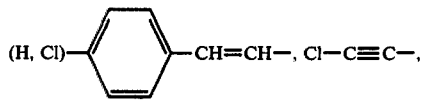

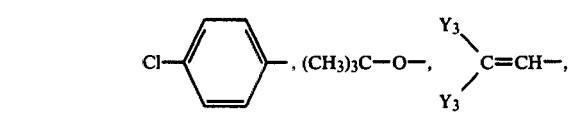

wherein Y₃ is chlorine, bromine, fluorine, —CF₃ or methyl, or A is CH₂=CH—CH₂—O— or

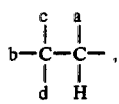

wherein each of a, b, c and d independently is chlorine, bromine or fluorine, whilst c and d can also be methyl, X is oxygen or sulfur, Y₁ is hydrogen, CN, CH₃, C₂H₅, i—C₃H₇,

—C≡CH, —C≡C—CH₃, —C≡C—C₆H₅, —CH=CH—CH₃, —CH₂—CH=CH₂, —CH=CH₂ or —CH₂—CH=CHCl, Y₂ is methyl or both of Y₂ together complete a cyclopropane, cyclobutane or cyclopentane ring and Y is

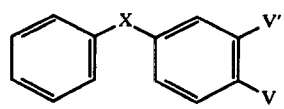

wherein V is hydrogen, chlorine, bromine, fluorine, methyl or nitro, or V' is CF₃ if V is hydrogen, and X is as defined above, or Y is

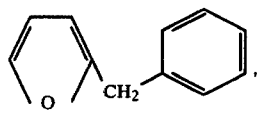

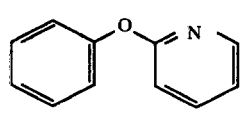, 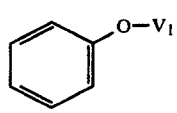

wherein V₁ is —CH₂—CH=CH₂, CH₂—C≡CH, —CH₂—CH=CH—CH₃,

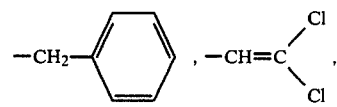

CF=CFCl or CF—CF₂, or Y is

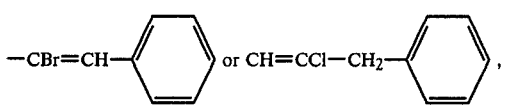

an ester of an α-alkyl-substituted phenylacetic acid of the formula

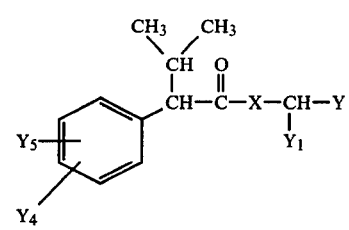

wherein X, Y and Y₁ are as defined above, Y₄ is hydrogen, CH₃, Cl, NO₂, OCH₃,

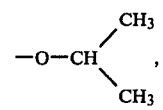

—O—CH₂—C≡CH or —O—CH₂—CH=CH₂, and Y₅ is hydrogen, methyl, chlorine, bromine or fluorine, or a substituted sulfanilide of the formula

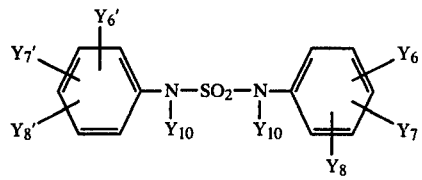

wherein each of Y₆, Y₇, Y₈, Y₆', Y₇' and Y₈' independently is hydrogen, chlorine, bromine, fluorine or CF₃, whilst each phenyl nucleus carries at least one substituent which is different from hydrogen and Y₁₀ is alkyl or aralkyl.

8. A method according to claim 7, which comprises treating the material to be protected with a mixture of a compound of the formula (1) and a compound from the class of the 3-(2',2'-dihalovinyl)-2,2-dimethylcyclopropanecarboxylic acid 3"-phenoxybenzyl esters, 3-(1',2',2',2'-tetrahaloethyl)-2,2-dimethylcyclopropanecarboxylic acid 3"-phenoxybenzyl esters, or of the α-phenyl-α-isopropylacetic acid 3'-phenoxybenzyl esters.

9. A method according to claim 8, which comprises treating the material to be protected with a mixture of a compound of the formula (1) and a compound of the formula

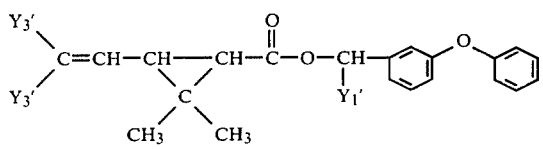

wherein $Y_3'$ is bromine, chlorine or methyl and $Y_1'$ is hydrogen or CN, or of the formula

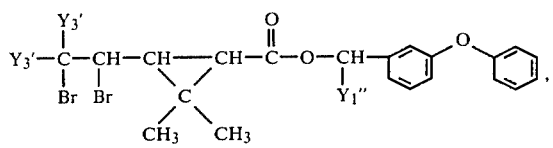

wherein $Y_3'$ is bromine, chlorine or methyl and $Y_1''$ is hydrogen, CN or —C≡CH, or of the formula

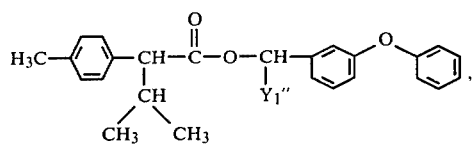

wherein $Y_1''$ is hydrogen, CN or —C≡CH.

10. A method according to either of claims 1 or 6, which comprises applying the active ingredients or mixtures to the material to be protected in an amount of 10 to 2000 ppm, based on said material.

11. A method according to claim 10, which comprises treating wool fabrics by the exhaust method in an aqueous liquor which contains the active ingredient or mixture and, with or without one or more dispersants or other dyeing assistants.

12. A method according to claim 10, which comprises treating wool fabrics by the pad method with an aqueous liquor which contains the active ingredient or mixture and, with or without one or more dispersants or other padding assistants.

13. A method according to either of claims 1 or 6, which comprises treating the material to be protected with an organic cleaning fluid which contains one or more of the compounds defined in claim 1 or mixtures defined in claim 6.

14. A method according to either of claims 1 or 6, which comprises spraying onto the material to be protected an organic solvent which contains one or more of the compounds defined in claim 1 or mixtures defined in claim 6.

15. A composition for protecting woollen goods, furs and skins against attack by moths and beetles, which contains one or more of the compounds of the formula (1) as defined in claim 1 and which additionally contains a synthetic pyrethoid, an ester or a thioester of an α-alkyl-substituted phenylacetic acid or a substituted sulfanilide.

16. A composition according to claim 15, which additionally contains a pyrethroid of the formula

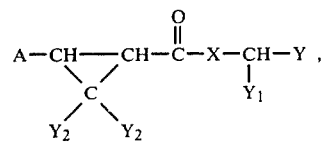

wherein A is $Br_2C=CBr—$,

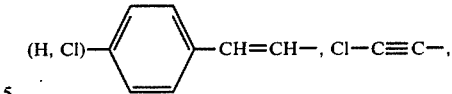

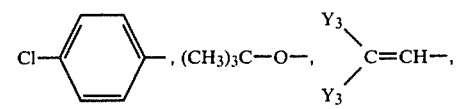

wherein $Y_3$ is chlorine, bromine, fluorine, —$CF_3$ or methyl, or A is $CH_2=CH—CH_2—O—$ or

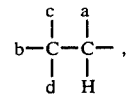

wherein each of a, b, c and d independently is chlorine, bromine or fluorine, whilst c and d can also be methyl, X is oxygen or sulfur, $Y_1$ is hydrogen, CN, $CH_3$, $C_2H_5$, i—$C_3H_7$,

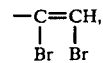

—C≡CH, —C≡C—$CH_3$, —C≡C—$C_6H_5$, —CH═CH—$CH_3$, —$CH_2$—CH═$CH_2$, —CH═$CH_2$ or —$CH_2$—CH═CHCl, $Y_2$ is methyl or both of $Y_2$ together complete a cyclopropane, cyclobutane or cyclopentane ring and Y is

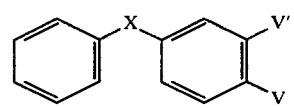

wherein V is hydrogen, chlorine, bromine, fluorine, methyl or nitro, or V' is $CF_3$ if V is hydrogen, and X is as defined above, or Y is

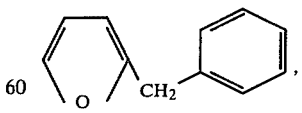

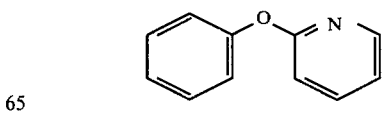

wherein $V_1$ is —$CH_2$—CH═$CH_2$, $CH_2$—C≡CH, —$CH_2$—CH═CH—$CH_3$,

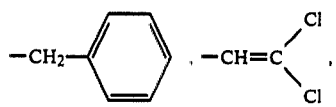

CF=CFCl or CF—CF₂; or Y is

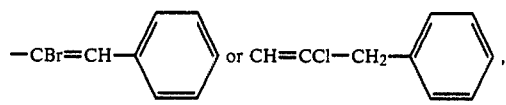

an ester of an α-alkyl-substituted phenylacetic acid of the formula

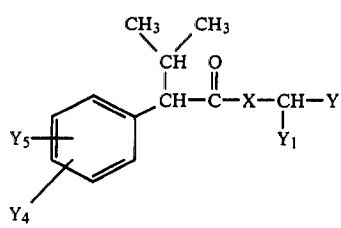

wherein X, Y and $Y_1$ are as defined above, $Y_4$ is hydrogen, $CH_3$, Cl, $NO_2$, $OCH_3$,

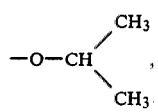

—O—$CH_2$—C≡CH or —O—$CH_2$—CH=$CH_2$, and $Y_5$ is hydrogen, methyl, chlorine, bromine or fluorine, or a substituted sulfanilide of the formula

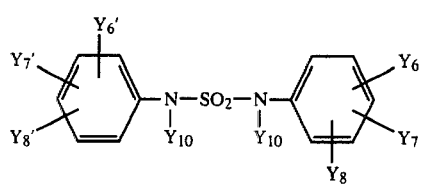

wherein each of $Y_6$, $Y_7$, $Y_8$, $Y_6'$, $Y_7'$ and $Y_8'$ independently is hydrogen, chlorine, bromine, fluorine or $CF_3$, whilst each phenyl nucleus carries at least one substituent which is different from hydrogen and $Y_{10}$ is alkyl or aralkyl.

17. A composition for protecting woollen goods, furs and skins against attack by moths and beetles, which contains one or more of the compounds of the formula (1) as defined in claim 1 and which additionally contains a compound from the class of the 3-(2',2'-dihalovinyl)-2,2-dimethylcyclopropanecarboxylic acid 3''-phenoxybenzyl esters, 3-(1',2',2',2'-tetrahaloethyl)-2,2-dimethylcyclopropanecarboxylic acid 3''-phenoxybenzyl esters, or of the α-phenyl-α-isopropylacetic acid 3'-phenoxybenzyl esters.

18. A composition for protecting woollen goods, furs and skins against attack by moths and beetles, which contains one or more of the compounds of the formula (1) as defined in claim 1 and which additionally contains a compound of the formula

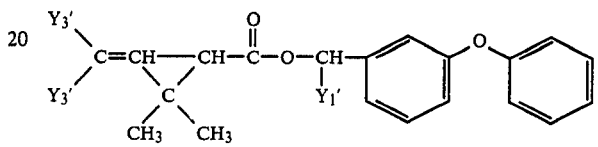

wherein $Y_3'$ is bromine, chlorine or methyl and $Y_1'$ is hydrogen or CN, or of the formula

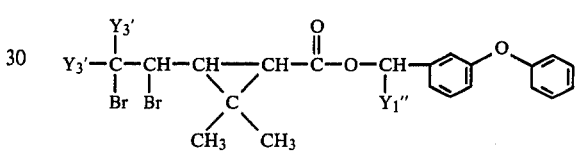

wherein $Y_3'$ is bromine, chlorine or methyl and $Y_1''$ is hydrogen, CN or —C≡CH, or of the formula

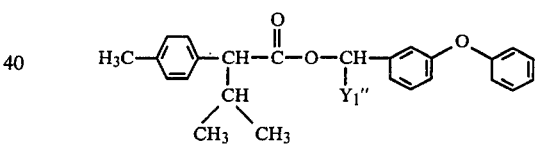

wherein $Y_1''$ is hydrogen, CN or —C≡CH.

19. A method according to claim 10, which comprises applying the active ingredients or mixtures to the material to be protected in an amount of 100 to 1000 ppm, based on said material.

* * * * *

UNITED STATES PATENT AND TRADEMARK OFFICE
CERTIFICATE OF CORRECTION

PATENT NO. : 4,283,444
DATED : AUGUST 11, 1981
INVENTOR(S) : BERNARDO DE SOUSA ET AL

It is certified that error appears in the above-identified patent and that said Letters Patent are hereby corrected as shown below:

Claim 2, Column 31, Lines 20-25, Formula reads:

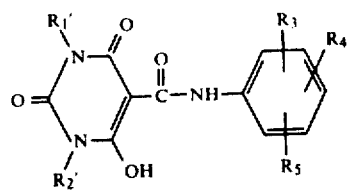

Should read:

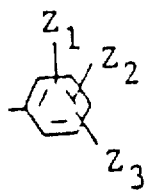

UNITED STATES PATENT AND TRADEMARK OFFICE
CERTIFICATE OF CORRECTION

PATENT NO. : 4,283,444
DATED : AUGUST 11, 1981
INVENTOR(S) : BERNARDO DE SOUSA ET AL

It is certified that error appears in the above–identified patent and that said Letters Patent are hereby corrected as shown below:

Claim 3, Column 31, Lines 55-60, Formula reads:

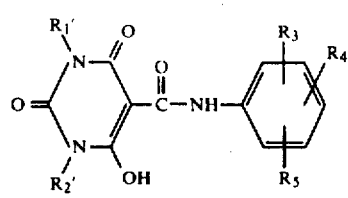

Should read:

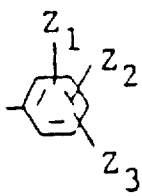

Signed and Sealed this

Twenty-sixth Day of January 1982

[SEAL]

Attest:

Attesting Officer

GERALD J. MOSSINGHOFF

Commissioner of Patents and Trademarks